United States Patent
Perrocheau et al.

(10) Patent No.: US 11,313,852 B2
(45) Date of Patent: Apr. 26, 2022

(54) METHOD AND PHARMACEUTICAL COMPOSITION FOR USE IN THE TREATMENT OF NEURODEGENERATIVE DISORDERS

(71) Applicants: Ludivine Perrocheau, Paris (FR); Alain Van Dorsselaer, Paris (FR); Jose Alain Sahel, Paris (FR); Thierry Leveillard, Paris (FR)

(72) Inventors: Ludivine Perrocheau, Paris (FR); Alain Van Dorsselaer, Paris (FR); Jose Alain Sahel, Paris (FR); Thierry Leveillard, Paris (FR)

(73) Assignees: INSERM Institut National de la Sante er de la Recherche Medicale, Paris (FR); CNRS CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 225 days.

(21) Appl. No.: 15/436,919

(22) Filed: Feb. 20, 2017

(65) Prior Publication Data
US 2017/0176417 A1    Jun. 22, 2017

Related U.S. Application Data

(63) Continuation of application No. 13/379,007, filed as application No. PCT/EP2010/058622 on Jun. 18, 2010, now abandoned.

(30) Foreign Application Priority Data

Jun. 19, 2009    (EP) .................................. 09305572

(51) Int. Cl.
*G01N 33/50*    (2006.01)
*A61K 38/52*    (2006.01)

(52) U.S. Cl.
CPC ......... *G01N 33/5058* (2013.01); *A61K 38/52* (2013.01); *G01N 33/5023* (2013.01); *G01N 2333/70596* (2013.01); *G01N 2800/28* (2013.01)

(58) Field of Classification Search
None
See application file for complete search history.

(56) References Cited

FOREIGN PATENT DOCUMENTS

AU    WO2006/084333    *    8/2006    .............. A61P 25/16

OTHER PUBLICATIONS

Ochrietor et al., Inactivation of the Basigin gene impairs normal retinal development and maturation. Vision Res. Feb. 2002;42(4):447-53.*
Peachey et al., Electrophysiological analysis of visual function in mutant mice. Doc Ophthalmol. Jul. 2003;107(1):13-36.*
Ochrietor et al., Retina-specific expression of 5A11/Basigin-2, a member of the immunoglobulin gene superfamily. Invest Ophthalmol Vis Sci. Sep. 2003;44(9):4086-96. (Year: 2003).*
Rivas et al., Animal models and different therapies for treatment of retinitis pigmentosa. Histology and histopathology (2009) 24: 1295-1322 (Year: 2009).*

* cited by examiner

*Primary Examiner* — Aurora M Fontainhas
(74) *Attorney, Agent, or Firm* — WC&F IP

(57) ABSTRACT

The invention relates to compounds which activate the BASIGIN signalling pathway, preferably agonists of BASIGIN, for the treatment of neurodegenerative disorders.

2 Claims, 3 Drawing Sheets

Figure 1:
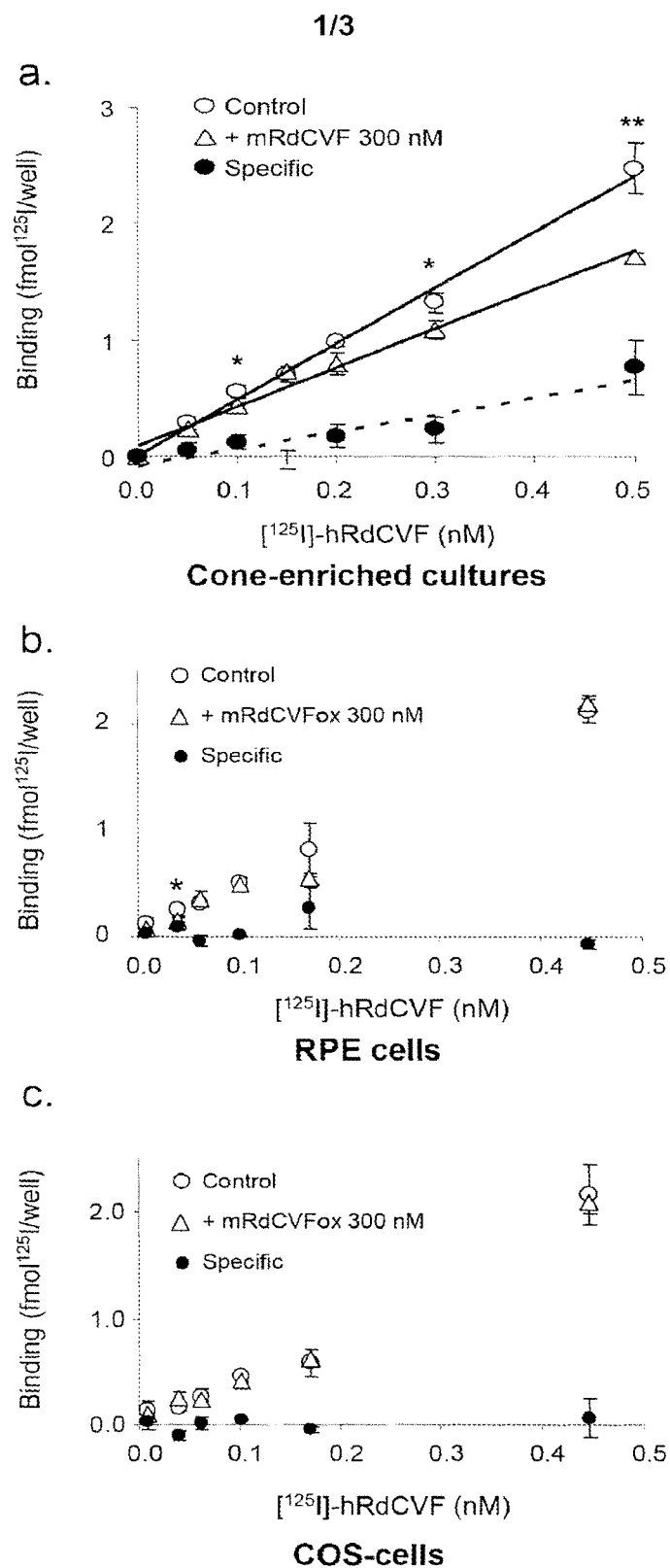

METHOD AND PHARMACEUTICAL COMPOSITION FOR USE IN THE TREATMENT OF NEURODEGENERATIVE DISORDERS

FIELD OF THE INVENTION

The invention relates to a compound which activates the BASIGIN signalling pathway for the treatment of a degenerative disorder. In particular, the invention relates to a BASIGIN agonist for the treatment of a neurodegenerative disorder.

BACKGROUND OF THE INVENTION

Neurodegenerative disorders have provided a challenge for many years, in both basic research and clinical contexts.

As an example of such a neurodegenerative disorder, retinitis pigmentosa (RP) is a genetically heterogeneous retinal degeneration characterized by the sequential degeneration of a population of neurons corresponding to rod and cone photoreceptors. The RP first clinical signs are night blindness and narrowing of the peripheral field of vision which progressively worsens to become "tunnel-like". Eventually, the central vision is reduced to complete blindness in most cases. At a cellular level, the retinal rod photoreceptors involved in night and side visions slowly degenerate. Subsequently, the cone photoreceptors responsible for both color and high-contrast vision, visual acuity, detail perception and normal light vision are similarly affected. The retinal degeneration 1 (rd1) mouse is the most studied animal model for retinitis pigmentosa. It carries a recessive mutation in the rod-specific cGMP phosphodiesterase beta subunit gene leading to rod photoreceptor death through apoptosis (Carter-Dawson et al., 1978; Portera-Cailliau et al., 1994) followed by cone death presumably through lack of trophic support (Mohand-Said et al., 1998).

The RdCVF gene, also called thioredoxin-like 6 (Txnl6) and nucleoredoxin 1 (Nxnl1), encodes the Q8VC33 UniProt protein, which has limited similarity to the thioredoxin superfamily and which exerts trophic activity on cone photoreceptors (Leveillard et al., 2004). Thioredoxins (TXN) are usually small proteins which can be involved with pleiotropic activities such as redox control, regulation of apoptosis and cytokine activity (Holmgren, 1985; Holmgren, 1989; ARNER and Holmgren, 2000). The TXN conserved active site contains two distinct cysteines (CXXC) that contribute to a thiol-oxydoreductase activity (Arner and Holmgren, 2000, Powis and Montfort, 2001) catalyzes the reduction of disulfide bonds in multiple substrate proteins (Holmgren, 1979; Holmgren, 1979). The RdCVF gene encodes two products via alternative splicing: a full length protein and a C-terminal truncated protein sharing similarities with TRX80. This latter form of human thioredoxin-1 (Txn) (Pekkari et al., 2000; Pekkari et al., 2005; Liu et al., 2005) has no thiol-reductase activity but is involved in controlling growth of peripheral mononuclear blood cells (Pekkari et al., 2000; Pekkari et al., 2003). Similar to Txn, RdCVF looks like a bifunctional gene because it encodes both a long form (RdCVF-L, 217 aa, Q8VC33) having a putative thiol-oxydoreductase activity (Jeffery, 1999; Jeffery, Trends Genet., vol. 19(8):415-417, 2003) and a short form (RdCVF-S, 109 aa, Q91W38) with trophic activity for cones but no redox activity. However the RdCVF receptor has not yet been identified.

There is still a need to find new compounds which can be used in the treatment of neurodegenerative disorders.

SUMMARY OF THE INVENTION

The inventors have now demonstrated that BASIGIN (also known as HT7, 5A11, EMMPRIN or CD147) is the RdCVF receptor.

A first object of the invention relates to a compound which activates the BASIGIN signalling pathway for the treatment of a neurodegenerative disorder.

Another object of the invention relates to a pharmaceutical composition for the treatment of a neurodegenerative disorder comprising a compound which activates the BASIGIN signalling pathway and a pharmaceutically acceptable carrier.

Yet another object of the invention relates to a method for screening a compound which activates the BASIGIN signalling pathway, in particular a BASIGIN agonist, for the treatment of neurodegenerative disorders.

Another object of the invention relates to the use of BASIGIN in a method for screening a drug for the treatment of a neurodegenerative disorder.

DETAILED DESCRIPTION OF THE INVENTION

Definitions

As used herein, the term "BASIGIN", also known as HT7/5A11/EMMPRIN/CD147, refers to a member of the immunoglobulin superfamily, with a structure related to the putative primordial form of the family (Miyauchi et al., 1991; Kanekura et al., 1991). BASIGIN is a type I integral membrane receptor that has many ligands, including the cyclophilin (CyP) proteins Cyp-A and CyP-B and certain integrins. It is expressed by many cell types, including epithelial cells, endothelial cells and leukocytes. The human BASIGIN protein contains 269 amino acids that form two heavily glycosylated C2 type immunoglobulin-like domains at the N-terminal extracellular portion. A second form of BASIGIN has also been characterized that contains one additional immunoglobulin-like domain in its extracellular portion.

As used herein, the term "compound which activates the BASIGIN signalling pathway" refers to a molecule which results in increased signalling through BASIGIN, whether by up-regulating the levels of BASIGIN present on the cell surface, or by stimulating the downstream signalling cascade by binding to BASIGIN. Methods for assessing the level of activation of the BASIGIN signalling pathway can include the measurement of the amount of downstream second messenger in the BASIGIN signalling pathway.

Compounds which activate the BASIGIN signalling pathway according to the invention include molecules which increase the levels of the BASIGIN protein on the cell surface, such as the BASIGIN polypeptide, a nucleic acid encoding BASIGIN, or a vector comprising a nucleic acid encoding BASIGIN.

Compounds which activate the BASIGIN signalling pathway can also include BASIGIN agonists. As used herein, the term "BASIGIN agonist" or "agonist of BASIGIN" refers to a molecule which activates signalling through the BASIGIN receptor, by binding to BASIGIN. Examples of such agonists of BASIGIN include, but are not limited to, cyclophilin A and cyclophilin B.

Typically, an agonist of BASIGIN according to the invention is not RdCVF1 or RdCVF2.

As used herein, the term "treating" or "treatment", means reversing, alleviating, inhibiting the progress of, or preventing the disorder or condition to which such term applies, or reversing, alleviating, inhibiting the progress of, or preventing one or more symptoms of the disorder or condition to which such term applies.

As used herein, the expression "neurodegenerative disorder" refers to a disease associated with the degeneration of neurons such as degenerative disorders of the central nervous system, retinal degenerative disorders, or degenerative disorders of the olfactory neurons. Typically, neurodegenerative disorders according to the invention include, but are not limited to, alcoholism, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Progressive Supranuclear Palsy, Refsum's disease, Sandhoff's disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and retinal degenerative disorders, Agonists and Uses Thereof A first object of the invention relates to a compound which activates the BASIGIN signalling pathway for the treatment of a neurodegenerative disorder.

In one embodiment, said compound which activates the BASIGIN signalling pathway is the human BASIGIN polypeptide referenced under Genpept accession number EAW61182 or a variant thereof having at least 90% identity with EAW61182, preferably 91%, 92%, 93%, 94%, 95%, 96%, 97%, 98%, 99% identity with EAW61182.

In another embodiment, said BASIGIN agonist is a nucleic acid encoding BASIGIN, or a vector comprising a nucleic acid encoding BASIGIN.

In a preferred embodiment, said compound which activates the BASIGIN signalling pathway is a BASIGIN agonist.

In one embodiment, said BASIGIN agonist may be a low molecular weight agonist, e.g. a small organic molecule (natural or not).

The term "small organic molecule" refers to a molecule (natural or not) of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

In another embodiment, BASIGIN agonist of the invention may consist in an antibody which activates BASIGIN or an antibody fragment which activates BASIGIN.

Antibodies directed against BASIGIN can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against BASIGIN can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-BASIGIN single chain antibodies. BASIGIN agonists useful in practicing the present invention also include anti-BASIGIN antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to BASIGIN.

Humanized anti-BASIGIN antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, BASIGIN agonists may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Another object of the invention relates to a method for treating a neurodegenerative disorder comprising administering to a subject in need thereof with a compound which activates the BASIGIN signalling pathway as described above.

In one aspect, the invention relates to a method for treating a neurodegenerative disorder comprising administering to a subject in need thereof a BASIGIN agonist as above described.

Compounds of the invention may be administered in the form of a pharmaceutical composition, as defined below.

Preferably, said compound which activates the BASIGIN signalling pathway, preferably said agonist of BASIGIN, is administered in a therapeutically effective amount.

By a "therapeutically effective amount" is meant a sufficient amount of compound to treat and/or to prevent neurodegenerative disorder.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Compounds according to the invention may be used for the preparation of a pharmaceutical composition for the treatment of a neurodegenerative disorder.

Hence, the present invention also provides a pharmaceutical composition comprising an effective dose of a compound which activates the BASIGIN signalling pathway, preferably a BASIGIN agonist, according to the invention.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Alternatively, compounds of the invention which activate the BASIGIN signalling pathway can be further identified by screening methods as hereinafter described.

Screening Methods

Another object of the invention relates to a method for screening a compound which activates the BASIGIN signalling pathway.

In particular, the invention provides a method for screening a BASIGIN agonist for the treatment of a neurodegenerative disorder.

For example, the screening method may measure the binding of a candidate compound to BASIGIN, or to cells or membranes bearing BASIGIN, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist).

Furthermore, screening methods may test whether the candidate compound results in a signal generated by an agonist of BASIGIN, using detection systems appropriate to cells bearing the receptor.

In a particular embodiment, the screening method of the invention comprises the step consisting of:
a) providing a plurality of neurons expressing BASIGIN on their surface:
b) incubating said neurons with a candidate compound;
c) determining whether said candidate compound binds to and activates BASIGIN; and
d) selecting the candidate compound that binds to and activates BASIGIN.

In one embodiment, the receptor BASIGIN used in the screening method may be its orthologs and derivatives as defined in the present invention.

In general, such screening methods involve providing appropriate cells which express BASIGIN, its orthologs and derivatives thereof on their surface. In particular, a nucleic acid encoding BASIGIN may be employed to transfect cells to thereby express the receptor of the invention. Such a transfection may be accomplished by methods well known in the art.

In a particular embodiment, neurons are selected from the group consisting of cone photoreceptor, neurons, retina cells, retinoblastoma and other immortalized neuronal cell lines of any species (mouse, human . . . ).

The screening method of the invention may be employed for determining an agonist by contacting such neurons with compounds to be screened and determining whether such compound activates the receptor.

The determination of the activation of BASIGIN can be assessed by determining the neuron viability. A compound is deemed to increase neuron viability if it is positive in any one the methods described below as examples of neuron rescue activity.

Alternatively, the determination of the activation of BASIGIN can be determined by analysing the downstream molecular signalling pathway. Indeed, it has been shown that stimulation of BASIGIN by cyclophilin A results in neuron protection via signalling through Erk1/2 (Boulos et al., Neurobiology of Disease, vol 25(1), p 54-64, 2007). Hence, determining the activation of BASIGIN can be carried our by monitoring the phosphorylation status of Erk.

According to a one embodiment of the invention, the candidate compound of may be selected from a library of compounds previously synthesised, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. Nos. 5,475,096 and 5,270,163. Further illustratively, the candidate compound may be selected from the group of antibodies directed against BASIGIN.

Such the method may be used to screen BASIGIN agonists according to the invention.

Furthermore, the invention relates to the use of BASIGIN polypeptide in a method for screening a drug for the treatment of neurodegenerative disorders.

The invention will be further illustrated by the following figures and examples.

FIGURES

FIG. 1: Specific binding for the cone-enriched culture: Iodinated human RdCVF peptide was incubated with a. cone-enriched cultures from chicken embryo, b. retinal pigmented epithelial cells from pig, c. Cos-1 cells. The dash line in a shows the specific binding after competition with the mouse unlabelled peptide FIG. 2: Purification of the RdCVF receptor by far-western blotting assay: Fractions from chicken retina and embryonic fibroblasts (CEF). S, solubles. M, membrane fractions. T total. Lane 2-4 coomassie staining. Lanes 5-14 farwestern blotting with GST-RdCVFL, GST-RdCVF and GST as indicated FIG. 3: Migration of the receptor BASIGIN on SDS-PAGE: Analysis by western blotting of retinal extracts (taken from published work)

EXAMPLES

Example 1

Specific Binding for the Cone-Enriched Culture

Material & Methods:

Human RdCVF (hRdCVF) and mouse RdCVF (mRdCVF) were synthesised at GeneProt and refolded (>90% purity). The chloramine T method was used to label hRdCVF with $^{125}I$ with a specific activity of 2130 Ci/mmol. Chick retina cells were isolated and cultured as previously described (Adler and Hatlee, 1989; Fintz et al, 2003) with minor modifications. The cells were plated on poly-L-lysine coated 24-well plates at $3\times10^5$ cells/cm$^2$ ($6\times10^5$/well) and cultured for 24 h in serum-containing medium. After 24 hours, the cells were rinsed three times then, 50 µl binding buffer (control) or 50 µl binding buffer containing unlabelled mRdCVF (to determine non-specific binding) was added to each well of the culture. After incubation for 30 min at room temperature, 50 µl binding buffer containing [$^{125}I$]-hRdCVF was added to each well. After incubation for 90 min at room temperature, the plates were incubated at 4° C. for 45 min. The cells were rinsed three times and solubilised with 1% SDS. The radioactivity of the extracts was counted using a gamma counter. The specific binding was measured by competition assay with excess unlabelled recombinant mouse RdCVF. The level of radioactivity was partially reduced by 300 nM unlabelled mRdCVF suggesting the presence of specific sites, despite saturation not being reached in the range of [$^{125}I$]-hRdCVF concentrations (0.05-0.5 nM, FIG. 2a). In three independent experiments, 300 nM mRdCVF inhibited 26% (2.4 fmol/well), 32% (1.2 fmol), and 31% (0.76 fmol) of the measured radioactivity at 0.5 nM [$^{125}I$]-hRdCVF.

Results:

In the absence of cells, we observed no inhibitory effect of mRdCVF suggesting that specific binding occurred on cells. We calculated a specific binding with a Kd of about 150 pM and a Bmax of 200 sites/cell. Cell differentiation seems to be involved because we could not detect RdCVF binding sites in fresh cell suspensions. Although the lack of binding of undifferentiated cells may be reflecting the specificity of the putative RdCVF receptor expression by cones, we address this directly by comparing the binding on chicken cones to that on primary retinal pigmented epithelial (RPE) cells from pigs. As RPE cells do not respond to RdCVF trophic activity, we expect them to show no specific RdCVF binding. The radioiodination of the synthetic RdCVF peptide was performed with an alternative protocol to that previously used (iodo-beads instead of lactoperoxydase). We have compared the binding of [$^{125}I$]-hRdCVF and the inhibitory effect of mouse RdCVF to cone-enriched cells from chicken retina, retinal pigmented epithelium (RPE) from pig and COS-1 cells. The non specific binding is linear for the three types of cells examined. Specific binding was observed only for the cone-enriched culture (FIG. 1). A comparison between [$^{125}I$]-hRdCVF binding and ATP content in four independent experiments show that there is a linear relationship between total binding and ATP. The IC50 was estimated to 35 nM (5.7 to 210 nM, 95% confidence limits). A rough estimation of the number of saturable binding sites, obtained by extrapolation of the binding parameters, gives 54,000 per cell (5,300 to 460,000, 95% confidence limits). This confirms that a specific binding activity for RdCVF is expressed by cones.

Example 2

Purification of the RdCVF Receptor by Far-Western Blotting Assay

Figure 2:
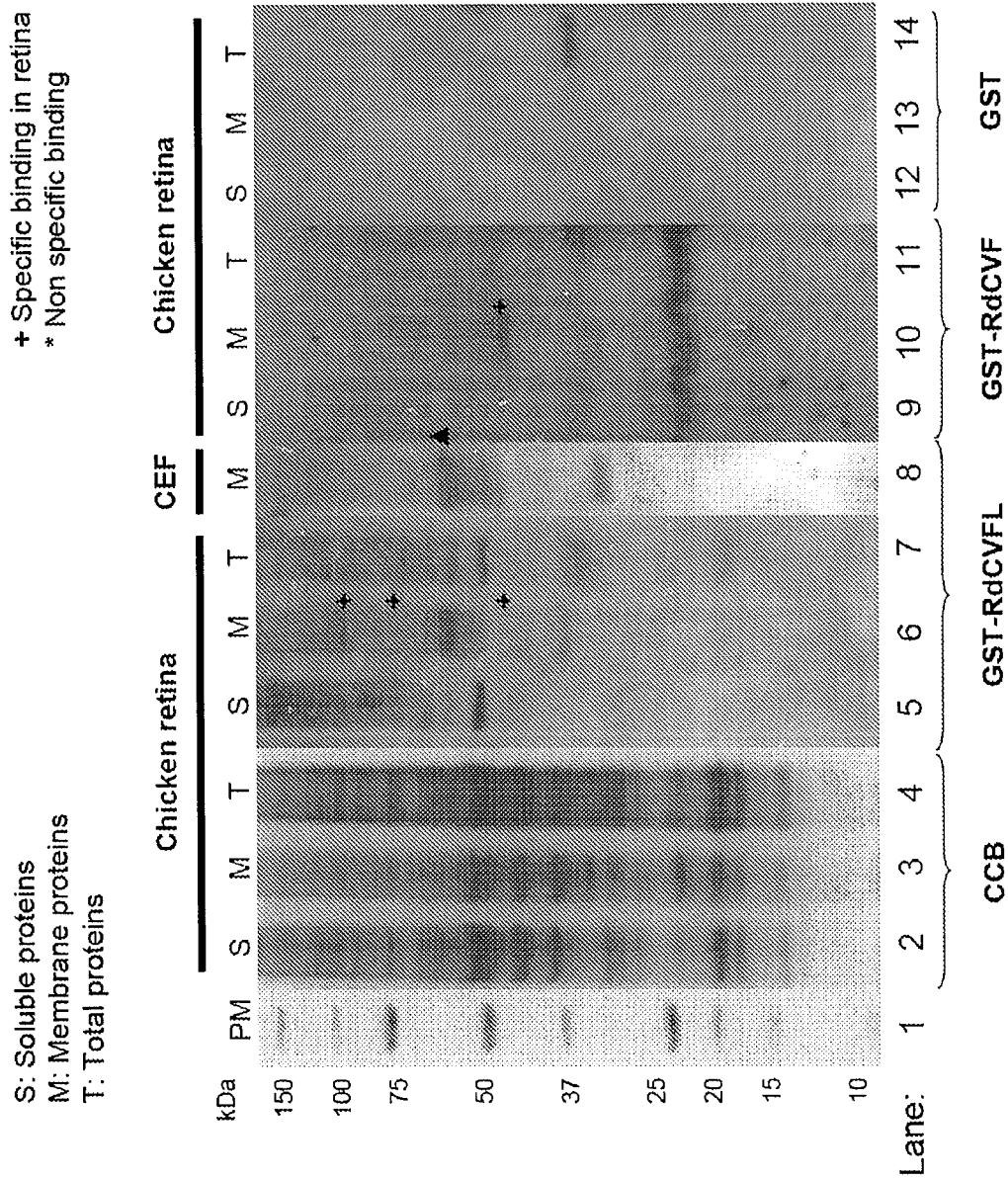

Material & Methods:

To purify the RdCVF receptor from the membrane fractions of the chicken retina, we have developed a far-western blotting assay (Léveillard et al., 1996). The protein fractions loaded onto an SDS gels are transferred onto nitrocellulose membranes. The denatured proteins on the membrane are then partially re-natured by serial incubation in buffer containing decreasing amounts of guanidine, the denaturing agent. The protein, used here as a probe, is produced in *E. coli* as a GST fusion in the vector pGEX2TK. We have previously shown that RdCVF protein produced using this vector system has a trophic activity toward chicken cones (Leveillard et al., 2004). This probe was applied to proteins on the membrane (FIG. 2).

Results:

We have looked for RdCVF-interacting proteins in the membrane and soluble fractions of chicken embryonic retina and test the tissue restricted expression using membrane fraction from chicken embryonic fibroblasts (CEF). We have used both the long and the short RdCVF proteins as probes as well as GST. When the protein GST was used as negative control, two non specific bands could be detected (*=37, 28 kDa in lane 14). Interestingly, several specific interacting proteins were found the membrane fractions of chicken retina (+~100, 75 and 45 kDa in lane 6 for GST-RdCVFL of chicken retina). The band at 50 kDa is likely corresponding to a soluble protein contaminating the membrane fraction since it is enriched in lane 5. The band at about 60 kDa, detected in lane 6, has a broader range of expression since it is also detected in the membrane fraction of chicken embryonic fibroblast (triangle in lane 8). Using the same extracts the short isoform detects a specific band smaller than 45 kDa in the membrane fraction of chicken retina (+in lane 10). The coomassie staining of these fractions shows that there is no prominent band at 45 kDa (lanes 2-4). Taken together these results indicate the existence of a candidate RdCVF interacting protein in the membrane fraction of the chicken retina migrating at 45 kDa. Additionally, while non quantitative, our assay shows that this interaction is of higher affinity with the short (lane 10) than that long (lane 6) isoform of RdCVF. We have shown that the trophic effect is mediated by the short and not the long isoform (Léveillard et al., 2004 and data not shown) reinforcing our interest in this 45 kDa protein.

We have performed a proteomic analysis of the band at 45 kDa from membrane fraction of chicken retina (lane 3). Because of the limited purification (membrane fractionation and SDS page), each band contains many proteins. A total of 144 proteins were identified using MS/MS for at least one matching peptide. The analysis of 111 proteins with sequence covered by at least 5%, shows that 58 proteins were identified as protein from the *Gallus gallus* genome and were considered for further analysis. Within that list, the presence of arrestin, vimentin and cone-type transducin alpha subunit signs the presence of retinal proteins within this fraction but also indicates that the protocol of purification does not allow removing all soluble proteins. A short list of 33 candidate proteins was established by removing unlikely candidates as the three retinal protein cited and other abundant and most likely contaminating proteins as enolase, creatine kinase, beta actin, mitochondrial ATPase, translation initiation factor, aldolase, Glucose 3P deshydrogenase, glucose phosphate isomerase, pyruvate kinase, heterogenous nuclear ribonucleoproteins as described in Casuvoglu et al. (2003). The abundance of proteins linked to the inner membrane of the cells as G-protein probably reflects the abundance of proteins associated with cell surface receptors in our preparation.

Among the list of 33 candidate proteins, 3 proteins containing a transmembrane domain (TM), a criterion that we have retained for the selection of a cell surface receptor. One of those was the cell surface glycoprotein HT7 precursor also known as BASIGIN (gi|69992).

Example 3

Migration of the Receptor BASIGIN on SDS-PAGE

Figure 3:
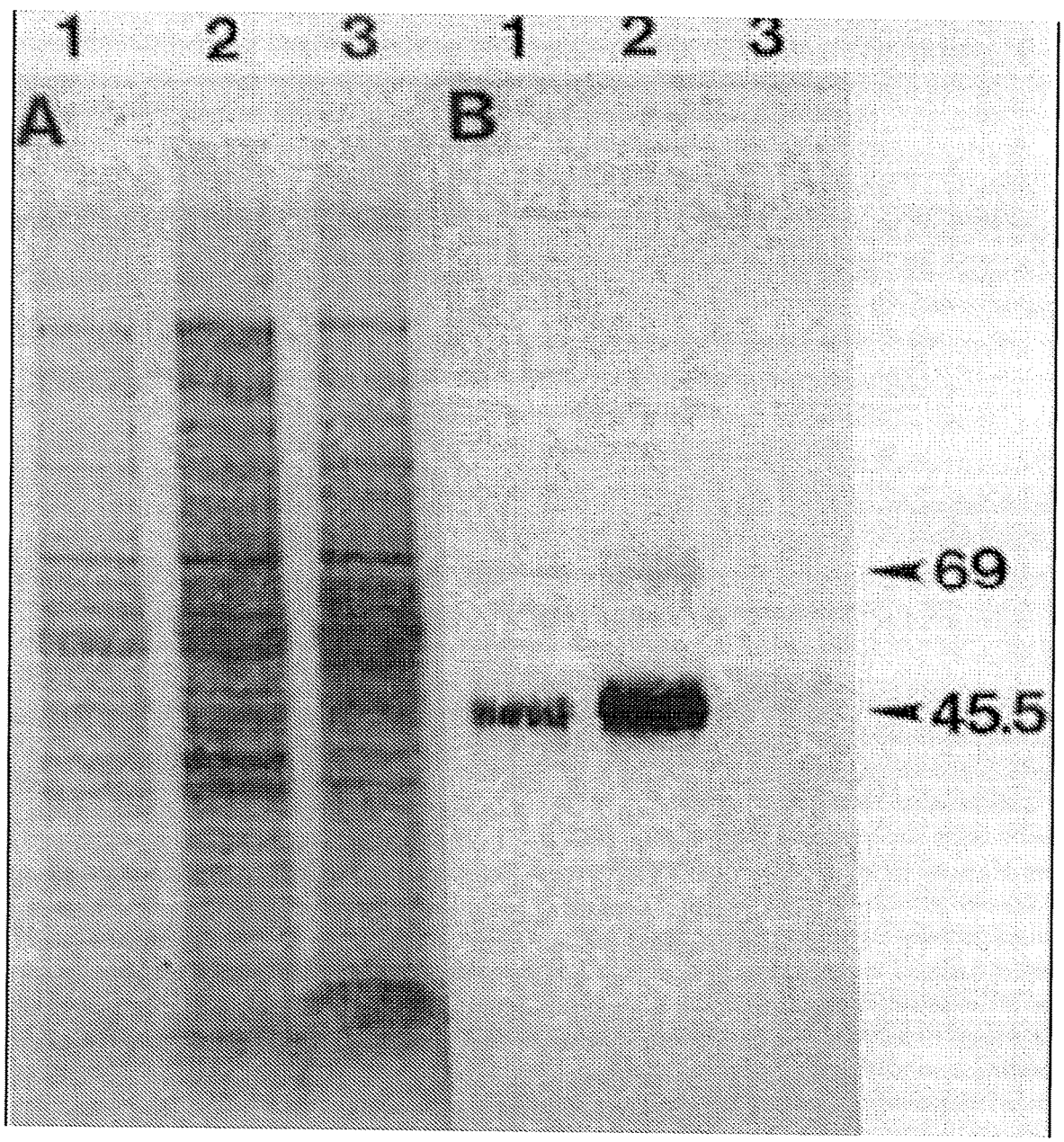

The cell surface glycoprotein BASIGIN was identified was originally identified as a blood brain barrier protein identical to the 5A11 antigen that mediates the cell-cell recognition in the avian retina (Fadool and Linser, 1993), a monoclonal antibody generated by immunizing mice with live cells dissociated from isolated day 7 embryonic chick retina (Linser and Perkins, 1987). Those cells are very similar to the day 6 embryonic chick retina used as cone-enriched culture system (Fintz et al., 2003; Léveillard et al., 2004). The migration of this glycoprotein on SDSPAGE is very similar to the RdCVF interacting protein as seen in a figure taken from the work of Fadool and Linser (FIG. 3). Interestingly, in that report the authors show that BASIGIN antibody (clone 5A11) inhibits retina cell reaggregation in vitro supporting the role of BASIGIN in cell-cell interactions. We have identified two clones encoding BASIGIN from an expression library constructed with RNA prepared from our cone-enriched cultures. The presence of these two clones out of a total of 1000 EST sequenced within the frame of an ongoing collaboration with the Génoscope (http://www.genoscope.cns.fr/spig/Mus-musculusdeqeneration-of.html) indicates that most likely BASIGIN is expressed by cones.

Example 4

Neuron Rescue Activity of BASIGIN Agonists

The BASIGIN agonists described in the present invention are tested for their ability to rescue neurons according to the following protocols:

1) Cone Rescue Activity

The primary culture is a cone-enriched primary cell culture system from chicken embryo (60-80% of cones) as described in Fintz et al. (Invest. Ophtamol. Vis. Sci, vol 44(2): 818-825, 2003.)

After 7 days of incubation with or without test compound, a period over which these post-mitotic cells degenerate, the viability of the cells in the culture is scored using the Live/Dead assay (Molecular Probes) and a cell counting platform as previously described (Leveillard et al., 2004).

2) Olfactory Sensitive Neuron Rescue Activity

Adult mice are killed by decapitation. The posterior part of the nasal septum is dissected free of the nasal cavity and immediately placed in ice-cold DMEM containing 50 µg/ml gentamicin (Eurobio; Gibco) and 10 (v/v) fetal calf serum (eurobio). The cartilage of the septum is removed and the olfactory mucosa is incubated for 30 min at 37° C. in a 2.4 U/Ml dispase II solution (Roche. The olfactory epithelium is carefully separated from the underlying lamina propria under the dissection microscope and gently triturated about 20 times to separate the cells. The resulting cell suspension is transferred to a 50 ml conical tube and the dispase is inactivated by adding 40 ml of HBSS without calcium and magnesium. The cell suspension is centrifuged at 700 rpm for 5 min, and the pellet containing the cells is resuspended in a medium composed of DMEM containing insulin (10 µg/ml, Sigma), transferin (10 µg/ml, Sigma), selenium (10 µg/ml, Sigma) calf foetal serum (5%), ascorbic acid (200 µM). Cells are plated on 12 mm sterile glass coverslips coated with 5 µg/cm$^2$ human collagen IV (Sigma); thus providing a primary culture of Olfactory Sensitive Neurons (OSN).

After 4 days of culture with or without test compound, cells are fixed and labelled with tubulin III, and counted.

3) Purkinje Cell Rescue Activity

After decapitation of mouse at postnatal day 1-3, brains are dissected out into cold Grey's balanced salt solution containing 5 mg/ml glucose, and the meninges are removed. Cerebellar parasagittal slices (35° or 250 µm thick) are cut on a McIlwain tissue chopper and transferred onto membrane of 30 mm Millipore culture inserts with 0.4 µm pore size (Millicel; Millipore, Bedford, Mass.). Slices are maintained in culture in 6-well plates containing 3 ml of medium at 35° in an atmosphere of humidified 5% $CO_2$. The medium is composed of 50% basal medium with Earle's salts (Invitrogen), 25% HBSS (Invitrogen), 25% horse serum (Invitrogen), L-glutamine (1 mM) and 5 mg/ml glucose (Stoppini et al., J Neurosci Methods, vol 37(2), p 173-82, 1991).

After 4 days of culture with or without test compound, cells are fixed and labelled with tubulin III, and counted.

4) Cortical Neuron Rescue Activity

Serum-free preparation of mouse cortical primary cultures is performed with mouse at postnatal day 1. After removal of the meninges, entire cortices are mechanically dissociated un a phosphate buffer saline glucose solution without added divalent cations (100 mM NaCl, 3 mM KCl, 1.5 mM KH2PO4, 7.9 mM Na2HPO4, 33 mM glucose, 100 U/ml penicillin and 100 µg/ml streptomycin) and resuspended in Neurobasal medium (Invitrogen) containing 2% B27 supplement (Gibco), 0.5 mM glutamine; and 25 µM glutamate. Cells are then cultured onto poly-ornithine coated coverslips to produce cultures highly enriched in cortical neurons.

After 4 days of culture with or without test compound, cells are fixed and labelled with tubulin III, and counted.

REFERENCES

Arner and Holmgren, Eur. J. Biochem., vol. 267(20), p: 6102-6109, 2000.
Carter-Dawson et al., Invest. Ophthalmol. Vis. Sci., vol. 17(6), p: 489-498, 1978.
Holmgren, J. Biol. Chem., vol. 254(18), p: 9113-9119, 1979.
Holmgren, J. Biol. Chem., vol. 254(19), p: 9627-9632, 1979.
Holmgren, Annu. Rev. Biochem., vol. 54, p: 237-271, 1985.
Holmgren, J. Biol. Chem., vol. 264(24), p: 13963-13966, 1989;
Jeffery, Trends Biochem. Sci., vol. 24(1):8-11, 1999.
Jeffery, Trends Genet., vol. 19(8):415-417, 2003.
Leveillard et al., Nat. Genet. vol. 36(7), p: 755-759, 2004).
Liu et al., Blood, vol. 105(4):1606-1613, 2005.
Mohand-Said et al., Proc. Natl. Acad. Sci. U.S.A, vol. 95(14), p: 8357-8362, 1998).
Pekkari et al., J. Biol. Chem., vol. 275(48), p: 37474-37480, 2000.
Pekkari et al., FEBS Lett., vol. 539(1-3):143-148, 2003.
Pekkari et al., Blood, vol. 105(4), :1598-1605, 2005.
Portera-Cailliau et al., Proc. Natl. Acad. Sci. U.S.A, vol. 91(3), p: 974-978, 1994.
Powis and Montfort, Annu. Rev. Pharmacol. Toxicol., vol. 41, p: 261-295, 2001.

The invention claimed is:

1. A method for screening BASIGIN pathway activating compounds for the treatment of a retinal neurodegenerative disorder comprising the steps of:
   a) providing a plurality of neurons expressing BASIGIN on their surface, wherein said neurons are cone photoreceptors, wherein said BASIGIN contains three immunoglobulin-like domains in its extracellular portion;
   b) incubating said neurons with a candidate compound;
   c1) determining whether said candidate compound binds to BASIGIN and
   c2) determining whether said candidate compound activates BASIGIN by:
      determining neuron viability, wherein an increased viability of neuron in a culture medium comprising the candidate compound compared to a control without candidate compound being indicative of an activation of BASIGIN; and/or
      analyzing a downstream molecular signaling pathway by measuring an intracellular ATP content, wherein an increased intracellular ATP content compared to a control without candidate compound being indicative of an activation of BASIGIN;
   thereby determining whether said candidate compound activates BASIGIN; and
   d) selecting the candidate compound that binds to and activates said BASIGIN.

2. The method of claim 1 wherein the retinal neurodegenerative disorder is retinitis pigmentosa.

* * * * *